United States Patent [19]

Jureller et al.

[11] Patent Number: 5,329,024
[45] Date of Patent: Jul. 12, 1994

[54] EPOXIDATION OF OLEFINS VIA CERTAIN MANGANESE COMPLEXES

[75] Inventors: Sharon H. Jureller, Haworth; Judith L. Kerschner, Ridgewood; Robert Humphreys, Oradell, all of N.J.

[73] Assignee: National Starch and Chemical Investment Holding Corporation, Wilmington, Del.

[21] Appl. No.: 40,316

[22] Filed: Mar. 30, 1993

[51] Int. Cl.$^5$ ............... C07D 301/06; C07D 301/12; C07D 301/14
[52] U.S. Cl. ............................ 549/531; 549/524; 549/525; 549/528; 549/533; 502/167
[58] Field of Search ............ 549/524, 525, 528, 531, 549/533

[56] References Cited

U.S. PATENT DOCUMENTS

| | | | |
|---|---|---|---|
| 4,892,941 | 1/1990 | Dolphin et al. | 549/524 |
| 5,126,464 | 6/1992 | Burrows et al. | 549/524 |
| 5,153,161 | 10/1992 | Kerschner et al. | 502/167 |

FOREIGN PATENT DOCUMENTS

| | | | |
|---|---|---|---|
| 342615 | 11/1989 | European Pat. Off. | 549/525 |
| 0458397 | 11/1991 | European Pat. Off. | |
| 0458398 | 11/1991 | European Pat. Off. | |

OTHER PUBLICATIONS

J. Am. Chem. Soc. (Weighardt et al) 1988, vol. 110, pp. 7398–7411.
J. Chem. Soc. Chem. Comm. (Weighardt et al) 1988, pp. 1145–1146.

*Primary Examiner*—Joseph E. Evans
*Attorney, Agent, or Firm*—Milton L. Honig

[57] ABSTRACT

A method for epoxidizing olefins is provided wherein an olefin and an oxygenating agent are contacted together in the presence of a manganese complex catalyst having at least one manganese atom coordinated with a nitrogen-containing ligand such that the manganese atom to coordinated nitrogen atom is 1:3 and thereafter isolating the resultant epoxide product. Catalyst compositions are also provided formed from the adsorption of the manganese complex catalyst onto a solvent insoluble support.

13 Claims, No Drawings

EPOXIDATION OF OLEFINS VIA CERTAIN MANGANESE COMPLEXES

BACKGROUND OF THE INVENTION

1. Field of the Invention

The invention relates to a method for epoxidizing olefins and catalysts employed therefor.

2. The Related Art

A variety of manganese compounds have been known for activating oxidation of unsaturated bonds. GB 2 225 963A (Casson et al) describes a manganese porphyrin supported on an inorganic substrate. The composition was indicated as useful for epoxidation of aromatics such as styrene. DE 34 38 484 (Rohde) describes the combination of a transition metal, phthalocyanine, and iodosobenzene as a useful epoxidation reagent.

JP 60 197 664A (Tabuse) reports epoxidation of polyenes through contact with a metal porphyrin, imidazole compound, platinum and hydrogen. Various solvents including water are suggested as effective media.

A problem with the known art is that metallo-porphyrin and phthalocyanine compounds are not readily soluble in aqueous media. Homogeneous catalysts is, therefore, problematical. Even in systems wherein manganese complexes operate heterogeneously, there remains room for yield and conversion improvements.

Accordingly, it is an object of the present invention to provide novel catalysts and a method for epoxidation of olefins which may be conducted homogeneously.

A further object of the present invention is to provide novel catalysts and a method for epoxidation of olefins which achieves improved yields and conversion over known catalytic systems.

These and other objects of the present invention will become more readily apparent from the detailed description and examples given hereafter.

SUMMARY OF THE INVENTION

A method of epoxidizing olefins is provided which includes the step of contacting the olefin in the presence of a manganese complex, the complex being formed from at least one manganese atom coordinated with a nitrogen-containing ligand such that a molar ratio of manganese to coordinated nitrogen atoms is 1:3, and the step of recovering epoxidized olefin. Epoxidation is best conducted in a fluid medium, especially an aqueous system.

A novel catalyst is also disclosed which includes a manganese complex formed from manganese coordinated with a nitrogen-containing ligand such that a molar ratio of manganese to coordinated nitrogen atoms is 1:3 and an inert substrate onto which the manganese complex is deposited.

DETAILED DESCRIPTION

Now it has been discovered that certain manganese complexes are highly effective at epoxidizing olefins. These complexes are formed from at least one manganese atom coordinated with a nitrogen-containing ligand such that a molar ratio of manganese to coordinated nitrogen atoms is 1:3.

Particularly preferred for purposes of this invention are mononuclear and dinuclear manganese complexes of Formulas (1) and (2), respectively. The structure of Formula (1) is as follows:

$$[LMnX_3]Y \quad (1)$$

wherein
- Mn is manganese;
- X is a coordinating species selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O_2^{2-}$, $HOO^-$, $H_2O$, $SH^-$, $CN^-$, $OCN^-$, and $S_4^{2-}$ and combinations thereof;
- R is a $C_1$–$C_{20}$ radical selected from the group consisting of alkyl, cycloalkyl, aryl, benzyl and radical combinations thereof;
- at least two R radicals may also be connected to one another so as to form a bridging unit between two oxygens that coordinate with the manganese;
- L is a ligand selected from a $C_3$–$C_{60}$ radical having at least 3 nitrogen atoms coordinating with the manganese; and
- Y is an oxidatively-stable counterion.

Counterion Y is usually an anion selected from the group consisting of: $Cl^-$, $Br^-$, $I^-$, $NO_3^-$, $ClO_4^-$, $NCS^-$, $PF_6^-$, $SO_4^{2-}$, $OAc^-$, $BPh_4^-$, $CF_3SO_3^-$, $RSO_3^-$, and $RSO_4^-$.

Preferred Formula (2) has the structure:

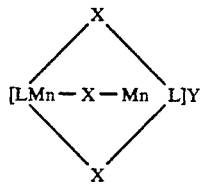

(2)

wherein Mn is manganese in a +III or +IV oxidation state and X, L and Y are as defined above.

The counterion Y needed for charge neutrality of the complex is generally provided by carrying out the complexation reaction in the presence of a counterion-forming salt. Though the type of the counterion-forming salt, e.g. chlorides; sulphates; nitrates; methylsulphates; and surfactants such as alkyl sulphates, alkyl sulphonates, alkylbenzene sulphonates, tosylates, trifluoromethyl sulphonates, perchlorates, $NaBH_4$ and $KPF_6$, is not critical for the conversion, some salts are more preferred than others in terms of product properties or safety. For example, small counterions will produce oily liquids and perchlorates are potentially explosive and could become a severe hazard upon large-scale preparation. Preferred counterions are the large molecules from surfactants, especially tosylate. A particularly preferred counterion is $PF_6^-$, which is conveniently obtained from $KPF_6$. Dinuclear manganese (III) and manganese (IV) complexes having $PF_6^-$ as the counterion, are solid crystalline products which are easy to handle and to form into a granulated catalyst product.

Ligands which are suitable for the present invention are for illustrative purposes only, listed through structural acyclic and cyclic formulas which follow:

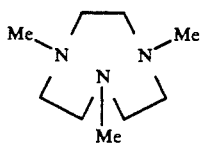

I

-continued

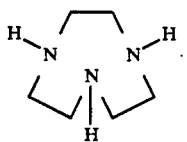

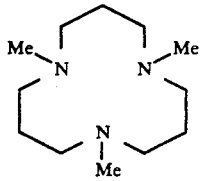

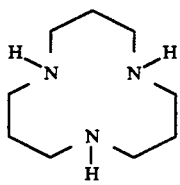

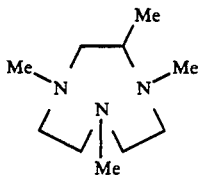

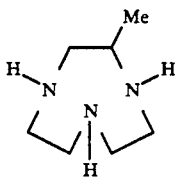

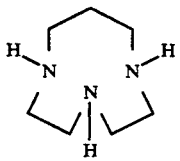

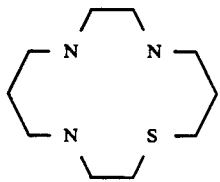

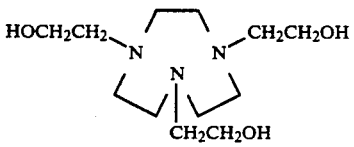

N,N',N''-(2-hydroxyethyl)-1,4,7-triazacyclononane

-continued

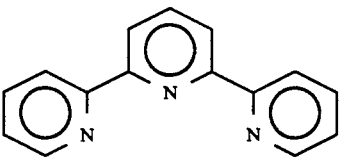

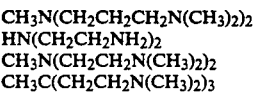

The most preferred ligands are I-V with I particularly preferred.

Ligand I is 1,4,7-trimethyl-1,4,7-triazacyclononane, coded as Me-TACN; ligand II is 1,4,7-triazacyclononane, coded as Me-TACN; ligand III is 1,5,9-trimethyl-1,5,9-triazacyclododecane, coded as Me-TACD; ligand V is 2methyl-1,4,7-trimethyl-1,4,7-triazacyclononane, coded as Me/Me-TACN; and ligand VI is 2-methyl-1,4,7-triazacyclononane, coded as Me/TACN; and ligand IX is N,N',N''-(2-hydroxyethyl)-1,4,7-triazacyclononane.

Illustrative of the most preferred mononuclear manganese complexes are the $SO_4^{2-}$ and $PF_6^-$ salts of Mn(IV)MeTACN(OMe)$_3$.

Most preferred of the dinuclear manganese complexes are those with the following structure:

[LMn(IV) (μ—O)$_3$Mn(IV)L]Y wherein L and Y are as described above.

Specifically preferred is a compound of the structure:

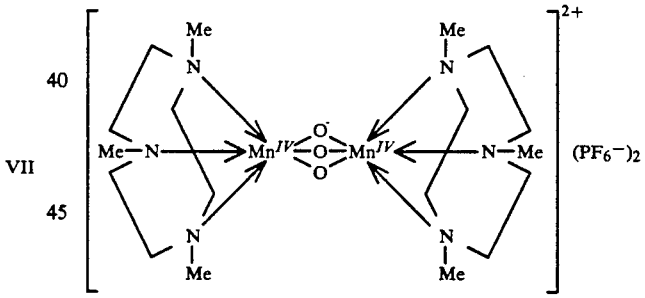

abbreviated as [Mn$^{IV}_2$(μ—O)$_3$ (Me—TACN)$_2$](PF$_6$)$_2$.

The mononuclear manganese complexes have previously been reported in copending U.S. application Ser. No. 07/798,396 filed Nov. 26, 1991. Several of the dinuclear manganese complexes were first synthesized and described by K. Wieghardt in the "Journal of American Chemical Society", 1988, Vol. 110, No. 22, page 7398, as well as in the "Journal of the Chemical Society—Chemical Communications", 1985, page 1145. Bleaching of laundry utilizing these complexes has also been described in EP 0 458 397 A2 and EP 0 458 398 A2 to Favre et al.

According to the present invention, the manganese complex may be utilized directly or as adsorbed onto a solvent insoluble support surface. Illustrative but non-limiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

A source of epoxidizing oxygen is also necessary for performing the claimed method. A wide variety of oxygen sources can be useful. These sources include oxygen, ozone, hydrogen peroxide, hydrogen peroxide-liberating compounds, hydrogen peroxide-generating systems, peroxyacids and their salts, and peroxyacid bleach precursor systems, as well as combinations thereof.

Hydrogen peroxide sources are well-known in the art. They include the alkali metal peroxides, organic peroxide bleaching compounds such as urea peroxide, and inorganic persalt bleaching compounds, such as the alkali metal perborates, percarbonates, perphosphates and persulphates. Mixtures of two or more of such compounds may also be suitable.

Organic peroxyacids suitable as the oxygen source are such materials having the general formula:

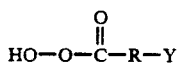

wherein R is an alkylene or substituted alkylene group containing from 1 to about 22 carbon atoms or a phenylene or substituted phenylene group, and Y is hydrogen, halogen, alkyl, aryl or

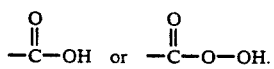

An essential element of the present invention is that of an olefin reactant containing unsaturated double bonds across which the epoxide may be formed. Suitable olefins include compounds with from 2 to 50 carbon atoms, preferably those having from 3 to 20 carbon atoms. They may be selected from mono- or multi-substituted, branched or unbranched alkenes and arylalkenes. Substitution of the alkenes may be in the form of hetero atom functional groups including those of halo, cyano, carboxylate, sulphate, phosphate, amino, hydroxyl, nitro, alkoxy, acyloxy and combinations thereof. The aforementioned functional groups are meant to be illustrative but nonlimiting examples. When the epoxidation process is conducted in an aqueous media, best results are obtained on olefins with water-soluble groups such as those with carboxylate and hydroxyl units, e.g. vinylbenzoic acid, styrylacetic acid and hexenoic acid.

A further listing of suitable olefins includes ethylene; propylene; α-olefins such as 1-octene and 1-decene and styrene; polyunsaturated olefins; acrylates such as methylmethacrylate; acrylamides such as methylolacrylamide; cyclic alkenes such as cyclooctene; terpenes; allylic compounds such as allyl chloride; vinyl compounds such as vinyl chloride; and acrylonitrile.

The relative weight ratio of manganese complex to olefin for purposes of the process may range anywhere from about 1:100,000 to about 1:50, preferably from about 1:1,000 to about 1:100.

Processes according to the present invention may either be batch or continuous. In the continuous mode, the manganese complex or a combination of complex adsorbed onto a support may be packed within a tubular column through which flows the olefin reagent or within a fluid bed reactor vessel. The process may be conducted in mono- or biphasic media. For instance, a biphasic media can be a combination of water and a water-insoluble organic solvent wherein the system is coupled through a phase transfer catalyst, (e.g. a quaternary ammonium salt) and/or a surfactant. The reaction may also be conducted neat utilizing the olefin reagent and epoxidized product as reaction media in the absence of extraneous solvent.

Typical aqueous or hydrophilic solvents for use in the invention besides water include $C_1$-$C_3$ alkanols (e.g. methanol or ethanol), ethylene or propylene glycol, polyethylene or polypropylene glycol, ethers (e.g. tetrahydrofuran, diethylether, glymes or cellosolves), dimethyl sulfoxide, dimethylformamide and acetonitrile. Hydrophobic solvents useful for the present invention include $C_3$-$C_{20}$ alkanes (e.g. hexane and petroleum ether), aromatics (e.g. benzene, toluene and xylene), halocarbons (e.g. chloroform, methylene chloride and chlorobenzene) and nitrobenzene.

Levels of oxidizing agent relevant to olefin may range from about 2:1 to about 10,000:1, optimally from about 500:1 to about 20:1. The most preferred relative ratio for hydrogen peroxide:olefin:manganese complex is about 10,000:100:1.

The following examples will more fully illustrate select embodiments of this invention. All parts, percentages and proportions referred to herein and in the appended claims are by weight unless otherwise indicated.

EXAMPLE 1

Typically the epoxidation reactions on a variety of olefins were conducted by adding the olefin (0.001 mol) to 90 ml of 0.1M $NaHCO_3$ buffer in water and the pH was adjusted to 9.0. Thereafter, 10 ml of 30% hydrogen peroxide (10M) was added thereto. Finally, 1.25 ml aliquot of 0.008M manganese complex was charged to start the reaction. Samples from the reaction were taken at intervals and analyzed by HPLC. Tables I and II sets forth a series of olefins with their epoxidation reaction times and % conversion rates.

TABLE I

| $Mn_2(Me_3TACN)_2(\mu\text{-}O)_3(PF_6)_2 \cdot H_2O$ | | |
|---|---|---|
| Olefin | % Conversion | Time |
| 4-Vinylbenzoic acid | 100 | 2 hrs. |
| Styrylacetic acid | 93 | 5 hrs. |
| Trans-3-Hexenoic acid | 100 | 22 hrs. |
| Trans-2-Hexenoic acid | 10 | 25 hrs. |

TABLE II

| $Mn(Me_3TACN)(OCH_3)_3(PF_6)$ | | |
|---|---|---|
| Olefin | % Conversion | Time |
| 4-Vinylbenzoic acid | 98 | 1.5 hrs. |
| Styrylacetic acid | 94 | 3 hrs. |
| Trans-3-Hexenoic acid | 69 | 28 hrs. |
| Trans-2-Hexenoic acid | 29 | 28 hrs. |

EXAMPLE 2

The catalytic epoxidation rates for several different manganese complexes were compared to one another as well as to hydrogen peroxide alone. These complexes were also compared with a typical Manganese (II) salt which is also known to catalyze the hydrogen peroxide oxidation of olefins. The experiments were performed in the same manner as in Example 1 with a catalyst:olefin:hydrogen peroxide ratio of 1:100:10,000 and the olefin was 4-vinylbenzoic acid. The results are shown in Table III.

TABLE III

4-Vinylbenzoic Acid

| Catalyst | % Conversion | Time |
|---|---|---|
| $Mn_2(Me_3TACN)_2(\mu\text{-}O)_3(PF_6)_2$ | 98 | 120 min. |
| $Mn(Me_3TACN)(OCH_3)_3(PF_6)$ | 96 | 90 min. |
| $Mn_2(Me_3TACN)_2(\mu\text{-}O)_2(\mu\text{-}O_2)(ClO_4)_2$ | 96 | 30 min. |
| $MnCl_2 + Me_3TACN$ | 97 | 60 min. |
| $Mn (EO_3TACN)(PF_6)$ | | |
| pH = 9.2 | 40 | 120 min. |
| pH = 8.5 | 100 | 90 min. |
| $MnCl_2$ | 96 | 240 min. |
| $H_2O_2$ alone | 19 | 255 min. |

As shown in Table III, all of the catalysts showed enhanced epoxidation rates over hydrogen peroxide alone or hydrogen peroxide plus Mn(II). Even addition of the ligand, $Me_3TACN$, to Mn(II) greatly enhanced the epoxidation rate suggesting in-situ formation of an active catalytic species.

EXAMPLE 3

The catalytic epoxidation rates of Mn(II) plus $Me_3$-TACN was compared to Mn(II) plus porphyrin ligands to compare the effectiveness of these complexes and this TACN ligand system. Manganese porphyrin complexes are known to catalytically epoxidize olefins. Accordingly, a water-soluble porphyrin, namely 4,4′,4″,4‴-(21H,23H-Porphine-5,10,15,20-tetrayl)tetrakis(benzoic acid), was added to Mn(II) and compared in-situ with Mn(II) plus $Me_3TACN$. The experiment was performed as described in Example 1 and the olefin epoxidized was 4-vinylbenzoic acid. The results are reported in Table IV.

TABLE IV

| Catalyst | % Conversion | Time |
|---|---|---|
| $MnCl_2 + Me_3TACN$ | 97 | 60 min. |
| $MnCl_2 + $ Porphyrin | 97 | 240 min. |
| $MnCl_2$ | 96 | 240 min. |

As the results indicate, the porphyrin ligand showed no enhanced reactivity over the Mn(II) salt. The $Me_3$-TACN ligand on the other hand exhibited a large enhanced rate of epoxidation over the Mn(II) compound.

EXAMPLE 4

This Example illustrates the use of $Mn_2(Me_3TACN)(\mu\text{-}O)_3(PF_6)_2$ for the epoxidation of allyl alcohol. The experimental protocol was as described in Example 1 and a catalyst:olefin:hydrogen peroxide ratio was kept constant at 1:100:10,000. The rate of epoxidation with catalyst was compared to the rate with hydrogen peroxide alone. The results are listed in Table V.

TABLE V

Allyl Alcohol

| Catalyst | % Conversion | Time |
|---|---|---|
| $Mn_2(Me_3TACN)_2(\mu\text{-}O)_3(PF_6)_2$ | 60 | 245 min. |
| $MnCl_2$ | 35 | 245 min. |
| $H_2O_2$ alone | 10 | 120 min. |

The foregoing description and examples illustrate selected embodiments of the present invention. In light thereof, various modifications will be suggested to one skilled in the art, all of which are within the spirit and purview of this invention.

What is claimed is:

1. A method of epoxidizing olefins comprising contacting an olefin with a source of oxygen and a manganese complex wherein a manganese atom is coordinated to a nitrogen-containing ligand such that there is a ratio of the manganese atom to coordinated nitrogen atoms in an amount of 1:3, and recovering subsequent thereto an epoxidized olefin.

2. A method according to claim 1 wherein a solvent is utilized as a reaction medium, the solvent being selected from the group consisting of hydrophobic and hydrophilic fluids.

3. A method according to claim 2 wherein the hydrophilic fluid is water.

4. A method according to claim 2 wherein the hydrophobic fluid is selected from the group consisting of hydrocarbons, halocarbons, nitrilohydrocarbons, aromatics and ethers.

5. A method according to claim 2 wherein the solvent has a structure with a functional unit selected from the group consisting of carboxylate, sulphate, phosphate, hydroxyl and a combination of units thereof.

6. A method according to claim 1 wherein the manganese complex has a formula selected from the group consisting of:

$$[LMnX_3]Y \qquad (1)$$

wherein

Mn is manganese;

X is a coordinating species selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O_2^{2-}$, $HOO^-$, $H_2O$, $SH^-$, $CN^-$, $OCN^-$, and $S_4^{2-}$ and combinations thereof;

R is a $C_1$–$C_{20}$ radical selected from the group consisting of alkyl, cycloalkyl, aryl, benzyl and radical combinations thereof;

at least two R radicals may also be connected to one another so as to form a bridging unit between two oxygens that coordinate with the manganese;

L is a ligand selected from a $C_3$–$C_{60}$ radical having at least 3 nitrogen atoms coordinating with the manganese; and Y is an oxidatively-stable counterion; and the formula:

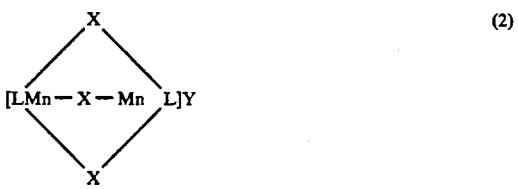

(2)

wherein Mn is manganese in a +III or +IV oxidation state and X, L and Y are as defined above.

7. A method according to claim 6 wherein the manganese complex has the formula $[Mn^{IV}_2 (\mu\text{---}O)_3 (MeTACN)_2] (PF_6)_2$.

8. A method according to claim 6 wherein the manganese complex has the formula $Mn(IV)(MeTACN)(OCH_3)_3(PF_6)$.

9. A method according to claim 6 wherein the ligand L is 1,4,7-trimethyl-1,4,7-triazacyclononane.

10. A method according to claim 6 wherein the ligand L is 2-methyl-1,4,7-trimethyl-1,4,7-triazacyclononane.

11. A method according to claim 6 wherein the ligand L is N,N',N''-(2-hydroxyethyl)-1,4,7-triazacyclononane.

12. A method according to claim 6 wherein Y is an anion selected from the group consisting of Cl$^-$, Br$^-$, I$^-$, NO$_3^-$, ClO$_4^-$, NCS$^-$, PF$_6^-$, SO$_4^{2-}$, OAc$^-$, BPh$_4^-$, CF$_3$SO$_3^-$, RSO$_3^-$, and RSO$_4^-$.

13. A method according to claim 1 wherein the oxygenating agent is selected from the group consisting hydrogen peroxide, hydrogen peroxide-liberating compounds, hydrogen peroxide-generating systems, peroxyacids and their salts, and peroxyacid bleach precursors, and mixtures thereof.

* * * * *